US00PP14112P29

(12) United States Plant Patent

Michalik

(10) Patent No.: US PP14,112 P2
(45) Date of Patent: Aug. 26, 2003

(54) VARIETY OF GERANIUM PLANT NAMED 'PENGRA'

(75) Inventor: Andrea Michalik, Dresden (DE)

(73) Assignee: Elser Pac Jungpflanzen (DE)

( * ) Notice: Subject to any disclaimer, the term of this patent is extended or adjusted under 35 U.S.C. 154(b) by 0 days.

(21) Appl. No.: 10/118,267

(22) Filed: Apr. 8, 2002

(51) Int. Cl.[7] ..... A01H 5/00
(52) U.S. Cl. ..... Plt./332
(58) Field of Search ..... Plt./327, 332

(56) References Cited

PUBLICATIONS

GTITM UPOVROM Citation for 'Granat' as per NL PBR GRM0210; Jun. 9, 1992.*
GTITM UPOVROM Citation for 'Granat' as per DE PBR PED 00039; Apr. 14, 1992.*

* cited by examiner

*Primary Examiner*—Kent Bell
(74) *Attorney, Agent, or Firm*—Webb Ziesenhiem Logsdon Orkin & Hanson, P.C.

(57) ABSTRACT

A new and distinct ivy geranium plant named 'Pengra' suitable for growth in a hanging basket and having shiny, intense red colored flowers which exhibit ivy-shaped leaves.

1 Drawing Sheet

Classification: *Pelargonium peltatum* (Ivy Geranium).
Varietal denomination: 'Pengra'.

BACKGROUND OF THE INVENTION

The present invention comprises a new and distinct cultivar of geranium known by the varietal name 'Pengra'. The new variety was discovered as a seedling in a selective breeding program in Dresden, Germany. The new variety is the result of a combination breeding of unnamed, unpatented selections from breeding group Granat 1999. The new variety exhibits the trailing growth of its heritage, but differs in its shiny intense red flower color and excellent branching. The new variety was first asexually reproduced by cuttings in Dresden, Germany in 2000. The new variety has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions via cuttings carried out in Dresden, Germany. The color readings were taken under natural light on plants grown in 19 cm. pots in greenhouses during summer. Plants for the description were 9 months old. Color references are primarily to The R.H.S. Colour Chart of The Royal Horticultural Society of London.

PLANT

Form: Trailing.
Height from media surface to top of foliage: 15 cm.
Height from media surface to top of umbels: 20 cm.

Time to produce a flowering plant: 16 weeks.
Growth: Well branched.
Strength: Hanging.
Roots: White, adventive, colored 155D, 3–4 weeks to develop.
Leaves: Opposite arrangement; zone present; some pubescence.
- *Length.*—3.5 cm.
- *Width.*—6.0 cm.
- *Shape.*—Overall: Ivy-shaped. Base: Cordate. Apex: Pointed.
- *Margin.*—Entire with occasionally slight serration.
- *Color.*—Upper surface: 137A with zone of 147A. Lower surface: 137D.

Ribs and veins:
- *Venation.*—Net-veined.
- *Color.*—137D.

Petioles:
- *Color.*—137C.
- *Length.*—3 cm.

Stem/branches:
- *Color.*—137C.
- *Overall stem length.*—60–70 cm.
- *Internode length.*—4–6 cm.
- *Lateral branch length.*—40 cm.

THE BUD (Described at first stage of opening)

Shape of individual bud: Oval.
Color: 46A.
Size:
- *Length.*—0.9 cm.
- *Width.*—0.5 cm.

INFLORESCENCE

Flowering: Begins early in summer and continues until frost.
Lasting quality:
- *Individual flowers.*—8–10 days.
- *Inflorescence.*—3–4 weeks.

Borne: Umbel; flowers on pedicel; pedicel on peduncle.
Umbel:
*Width.*—7–8 cm.
*Depth.*—4 cm.
*Number of flowers per umbel.*—6–10.
Flowers:
*Form.*—Zygomorph, semi-double.
*Size.*—Diameter: 4.5 cm. Depth: 1.5 cm.
*Petals.*—Quantity: 9–11 per flower. Color: Upper surface: 46A with markings of 53A. Lower surface: 45D. Eye: Upper petals have markings colored 53A. Size: Length: 2.0–2.5 cm. Width: 1.3–1.6 cm. Shape: Overall: Oval. Apex: Round. Base: Pointed. Margin: Entire. Texture: Smooth.
Petaloids: 3–4, irregular shape.
*Color.*—Upper surface: 46A with 53A markings. Lower surface: 45D.
Sepals:
*Shape.*—Overall: Narrow. Apex: Pointed. Base: Fused.
*Color.*—Upper surface: 137C. Lower surface: 137C.
*Size.*—Length: 1.2 cm. Width: 0.5 cm.
Pedicel:
*Length.*—2–2.5 cm.
*Color.*—137B.
Peduncle:
*Length.*—10–12 cm.
*Color.*—137B.
Disease/pest resistance: No susceptibility to diseases or pests noted to date.

REPRODUCTIVE ORGANS

Stamens:
*Anthers.*—3 mm long.
*Filaments.*—Length: 8 mm. Color: 43D.
*Pollen color.*—32B.
Pistils:
*Number.*—One; 5–7 parted.
*Length.*—3–4 mm.
*Stigma color.*—59B.
*Style.*—Length: 8 mm. Color: 75D.
Ovaries: Superior, hairy.
*Length.*—5 mm.
*Color.*—136D.
Fruit: If present, maximum 5 per flower, 0.3–0.4 cm long, colored 165A.

GENERAL CHARACTERISTICS

1. Shiny, intense scarlet flower color.
2. Trailing with good branching.
3. Good rooting.
4. Heat tolerant.
5. Stable flower color.

I claim:

1. A new and distinct variety of geranium plant substantially as shown and described.

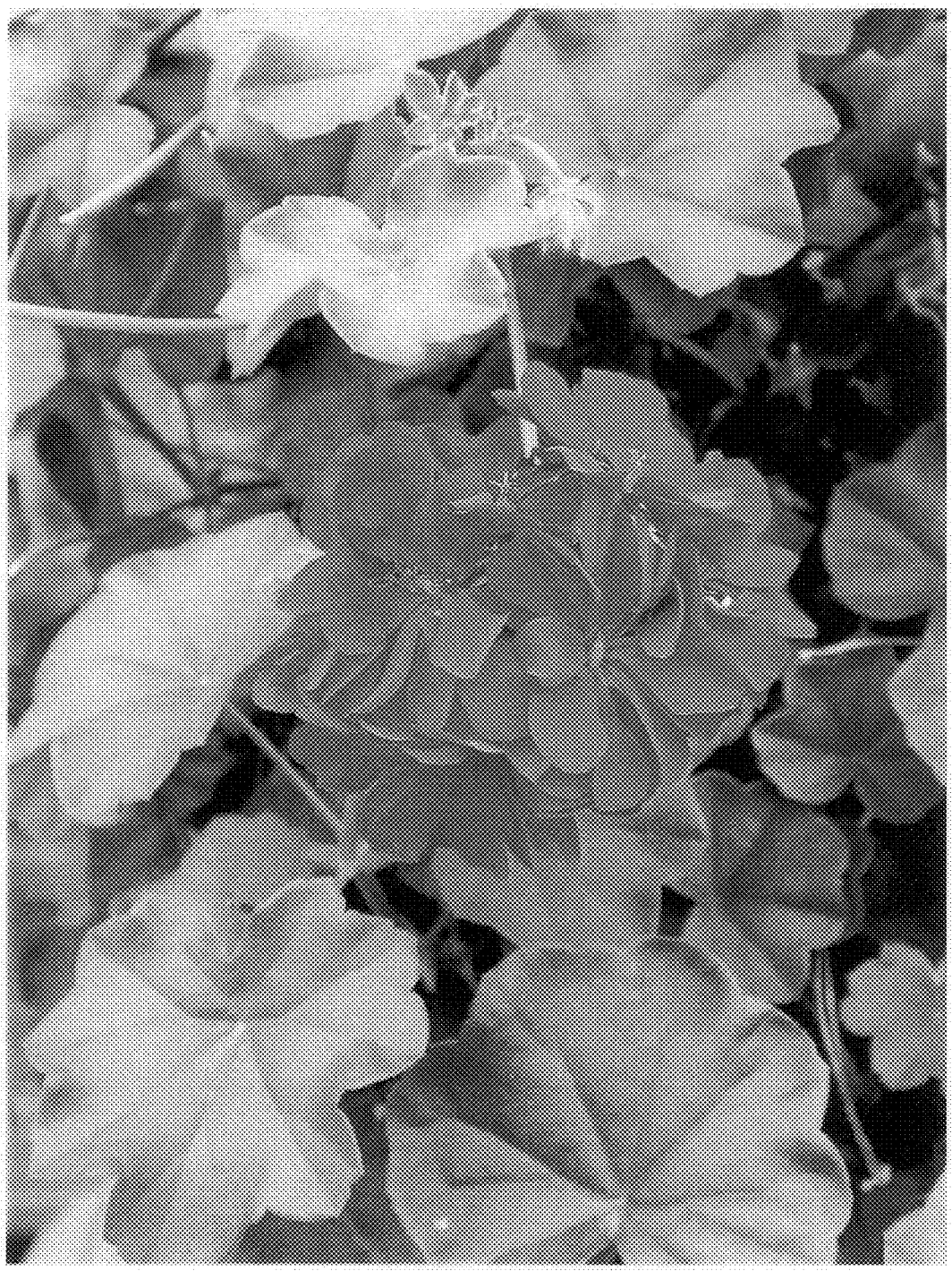

* * * * *